US012570624B2

(12) United States Patent
Das et al.

(10) Patent No.: US 12,570,624 B2
(45) Date of Patent: Mar. 10, 2026

(54) METAL CATALYST AND HYDROGEN GAS FREE APPROACHES FOR SELECTIVE REDUCTION OF ALDEHYDE TO METHYL GROUP OF DIFFERENT SUBSTITUTED FURANS

(71) Applicant: COUNCIL OF SCIENTIFIC AND INDUSTRIAL RESEARCH, New Delhi (IN)

(72) Inventors: Pralay Das, Himachal Pradesh (IN); Arvind Singh Chauhan, Himachal Pradesh (IN); Ajay Kumar, Himachal Pradesh (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 875 days.

(21) Appl. No.: 17/800,701

(22) PCT Filed: Feb. 19, 2021

(86) PCT No.: PCT/IN2021/050157

§ 371 (c)(1),
(2) Date: Aug. 18, 2022

(87) PCT Pub. No.: WO2021/165991

PCT Pub. Date: Aug. 26, 2021

(65) Prior Publication Data

US 2023/0348409 A1 Nov. 2, 2023

(30) Foreign Application Priority Data

Feb. 19, 2020 (IN) ............................ 202011007068

(51) Int. Cl.
*C07D 307/48* (2006.01)
*C07D 307/36* (2006.01)
*C11C 3/12* (2006.01)

(52) U.S. Cl.
CPC ......... *C07D 307/48* (2013.01); *C07D 307/36* (2013.01); *C11C 3/126* (2013.01)

(58) Field of Classification Search
CPC .................................................... C07D 307/48
See application file for complete search history.

(56) References Cited

U.S. PATENT DOCUMENTS 4,590,283 A * 5/1986 Gaset .................. C07D 307/46 549/488
11,440,894 B2 * 9/2022 Das ...................... C07D 307/50

OTHER PUBLICATIONS

Mika, et al., "Catalytic Conversion of Carbohydrates to Initial Platform Chemicals: Chemistry and Sustainability", Chemical Reviews, vol. 118, pp. 505-613, 2018.

Li, et al., "Acid-Base Bifunctional Zirconium N-Alkyltriphosphate Nanohybrid for Hydrogen Transfer of Biomass-Derived Carboxides", American Chemical Society, vol. 6, pp. 7722-7727, 2016.

Li, et al., "Selective Deoxygenation of Aqueous Furgural to 2-Methylfuran over $Cu^0/Cu_22O$—$SiO_2$ Sites via a Copper Phyllosilicate Precursor without Extraneous Gas", ACS Sustainable Chem. Eng., vol. 6, pp. 12096-12103, 2018.

He, et al., "Catalytic Transfer Hydrogenation of Bio-Based Furfural with NiO Nanoparticles", ACS Sustainable Chem. Eng., vol. 6, pp. 17220-17229, 2018.

Thananatthanachon, et al., "Efficient Production of the Liquid fuel 2,5-Dimethylfuran from Fructose Using Formic Avid as a Reagent", Angew. Chem., vol. 122, pp. 6766-6768, 2010.

Zheng, et al., "An environmentally benign process for the efficient synthesis of cyclohexanone and 2-methylfuran", Green Chem., vol. 8, pp. 107-109, 2006.

Chatterjee, et al., "Selective hydrogenation of 5-hydroxymethylfurfural to 2,5-bis-(hydroxymethyl)furan using Pt/MCM-41 in an aqueous medium: a simple approach", Green Chemistry, vol. 16, pp. 4734-4739, 2014.

Upare, et al., "An integrated process for the production of 2,5-dimethylfuran from fructose", Green Chemistry, vol. 17, pp. 3310-3313, 2015.

Chen, et al., "Perovskite type oxide-supported Ni catalysts for the production of 2,5-dimethylfuran from biomass-derived 5-hydroxymethylfurfural", Green Chemistry, vol. 18, pp. 3858-3866, 2016.

Han, et al., "Heterogeneous zirconia-supported ruthenium catalyst for highly selective hydrogenation of 5-hydroxymethyl-2-furaldehyde to 2,5-bis(hydroxymethyl)furans in various n-alcohol solvents", RCS Advances Communication, vol. 6, pp. 93394-93397, 2016.

Upare, et al., "An integrated process for the production of 2,5-dimethylfuran from fructose", Green Chemistry, vol. 20, pp. 879-885, 2018.

Liu, et al., "Effects of Water on the Copper-Catalyzed Conversion of Hydroxymethylfurfural in Tetrahydrofuran", ChemSusChem, vol. 8, pp. 3983-3986, 2015.

Li, et al., "Orderly Layered Zr-Benzylphosphonate Nanohybrids for Efficient Acid-Base-Mediated Bifunctional/Cascade Catalysis", ChemSusChem, vol. 10, pp. 681-686, 2017.

Dong, et al., "Cr-free Cu-catalysts for the selective hydrogenation of biomass-derived furfural to 2-methylfuran: the synergistic effect of metal and acid sites", Journal of Molecular Catalysis A: Chemical, pp. 1-25, 2014.

Nishimura, et al., "Selective hydrogenation of biomass-derived 5-hydroxymethylfurfural (HMF) to 2,5-dimethylfuran (DMF) under atmospheric hydrogen pressure over carbon supported PdAu bimetallic catalyst", Catalysis Today, vol. 232, pp. 89-98, 2014.

* cited by examiner

*Primary Examiner* — Golam M Shameem

(74) *Attorney, Agent, or Firm* — DINSMORE & SHOHL LLP

(57) ABSTRACT

The present invention relates to 5-methyl substituted furan compounds of general formula (I) and process for the preparation thereof: OR1R2 R3CH3 (I) Particularly, the present invention relates to a metal catalyst and hydrogen gas free, atom-economy, highly selective and low-cost process for the preparation of methyl substituted furan compounds from different aldehyde substituted furan compounds.

20 Claims, No Drawings

METAL CATALYST AND HYDROGEN GAS FREE APPROACHES FOR SELECTIVE REDUCTION OF ALDEHYDE TO METHYL GROUP OF DIFFERENT SUBSTITUTED FURANS

CROSS REFERENCES TO RELATED APPLICATIONS

This application is a national-stage application under 35 U.S.C. § 371 of International Application No. PCT/IN2021/050157, filed Feb. 19, 2021, which International Application claims benefit of priority to Indian Patent Application number 202011007068, filed Feb. 19, 2020.

FIELD OF THE INVENTION

The present invention relates to a 5-methyl substituted furan compound of general formula (I) and a process for the preparation thereof:

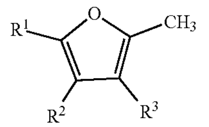

(I)

wherein;

$R^1$ is selected from the group comprising: hydrogen, hydroxymethyl, methyl, alkyl, hydroxy, aldehyde, halide, ester, carboxylic acid, amide, amine, substituted amine, alkoxy/ether linkages, sulphur derivatives, phosphorous derivatives and any aryl and hetero aryl functionality; and $R^2$ and $R^3$ may be selected from the group comprising: hydrogen, alkyl, and aryl.

More particularly, the present invention relates to a new protocol for "Metal free approaches for selective reduction of aldehyde to methyl group of differently substituted furans". A metal catalyst free and hydrogen gas free, atom-economy, highly selective and low-cost process has been developed by the present invention for the preparation of methyl substituted furan compounds from different aldehyde substituted furan compounds. The process steps are easy to scale-up and no need of tedious purification steps to achieve high purity.

The present invention particularly relates to a process for preparation of 5-methyl furfuryl alcohol (5-MFA), 2,5-dimehtyl furan (DMF), 5-methyl furan from their corresponding aldehyde compounds, having huge application as bio-fuel and other applications.

The present invention further relates to methyl substituted furan compounds of general formula (I) useful as an intermediate/final product for the production of bio-fuel, fragrances, food additives, pharmaceuticals, resin and biopolymer synthesis.

The present invention further relates to a convenient, inexpensive, efficient and scalable method for the synthesis of methyl substituted furan compounds of general formula (I).

BACKGROUND OF THE INVENTION

The biomass derived bio-fuel production has become hot and important issue over the last few decades. Day by day, the depletion of fossil-based resources and emission of greenhouse gases has forced the research world to utilize renewable resources as feedstock for bio-fuel production. The biomass resources (lignocellulose, cellulose, starch, fructose, glucose, sucrose etc.) have been assumed as renewable resources for production of energy and fine bulk chemicals as these resources are widely abundant in nature. The 5-hydroxymethylfurfural (HMF) is considered a platform molecule in this context; derived from biomass acting as key intermediate for production of various fine chemicals and bio-fuels (Mika, L. T., Cséfalvay, E. and Németh, A., *Chem. Rev.,* 2018, 118, (2), 505-613).

The reduction of 5-HMF afforded 2,5-dimethylfuran (DMF) which is a promising bio-fuel derived from 5-HMF as well as directly from biomass. An industrial scale production of bio-fuels still need high scientific interventions because of its high cost processing and scale up issues. In this regard, 5-methylfurfuryl alcohol (5-MFA) is envisaged as an important intermediate which undergo hydrogenolysis to give dimethylfuran (bio-fuel) (Thananatthanachon, T. and Rauchfuss, B. T., *Angew. Chem.,* 2010, 49, 6616-6618). Nishimura et al. has been reported the hydrogenation of 5-HMF to 2,5-DMF through the 5-MFA intermediate with Pd-Au/C catalyst. The yield of 5-MFA production under this condition is very low (Nishimura, S.; Ikeda, N. and Ebitani, K., *Catalysis Today,* 2014, 232, 89-98). 5-Chlorofuran-2-carbaldehyde was also reported as a precursor for 5-MFA synthesis (GC quantitative yield 98%) by using Zr-benzylphosphonate (Li, H.; Fang, Z.; He, J. and Yang, S., *ChemSusChem,* 2017, 10, 681-686). Moreover, the 5-MFA also played significant role for 2,5-DMF synthesis using Cu/g-$Al_2O_3$ and molecular hydrogen as a hydrogen source. The effect of water on Cu/g-$Al_2O_3$ was explained and found that in the absence of water, primary hydrogenolysed product of 5-HMF was 5-MFA and 2,5-DMF (Liu, Y.; Mellmer, A. M.; Alonso, M. D. and Dumesic, A. J., *ChemSusChem,* 2015, 8, 3983-3986). In continuation of this development, various heterogeneous catalytic approaches have also been applied such as zirconia supported ruthenium catalyst (Ru (OH)x/$ZrO_2$) for highly selective hydrogenation of 5-HMF to 2,5-BHMF in various alcoholic solvents and it was observed that in case of 2-propanol and tertiary butyl alcohol, the 5-MFA was formed as a by-product (Han, J.; Kim, H. Y.; Jnag, S. H.; Hwang, Y. S.; Jegal, J.; Kim, W. J. and Lee, S. Y., *RSC Adv.,* 2016, 6, 93394-93397). Later on, $Cu_{(50)}$-$SiO_2$ nanocomposite was also developed for the DHMF synthesis from 5-HMF. The formation of 5-MFA (2%) was reported along with DHMF (Upare, P. P.; Hwang, K. Y. and Hwang. W. D., *Green Chem.,* 2018, 20, 879-885). The maximum yield of 5-MFA (19%) was obtained by using Ru-Sn/ZnO (Upare, P. P.; Hwang, W. D.; Hwang, K. Y.; Lee. H. U.; Hong, Y. D. and Chang, S. J., *Green Chem.,* 2015, 17, 3310-3313). Nickel supported on perovskite type oxide was screened as well by Fu et al. and observed that 5-MFA (38.5%) was formed along with other hydrogenolysed product of 5-HMF (Chen, Y. M.; Chen, B. C.; Zada, B. and Fu, Y., *Green Chem.,* 2016, 18, 3858-3866). Another approach attempted for the synthesis of BHMF from 5-HMF by Chatterjee et al. by hydrogenation under mild reaction conditions; hydrogen pressure 0.8 MPa in an aqueous media using catalyst Pt/MCM-41 without any additives. It was observed that the 5-MFA (GC yield 90%) produced only when the substrate is methyl furfural and BHMF, also the enhancement in reaction time from standard conditions (from 2 hr to 6 hr) would favour 5-MFA formation (Chatterjee, M.; Ishizaka, T. and Kawanami, H., *Green Chem.,* 2014, 16, 4734-4739). Recently, Hu et al. has performed the catalytic transfer hydrogenation of 5-methylfurfural into 5-methyl furfuryl alcohol with Zirconium N-alkyltriphosphate nanohybrid (ZrPN) at 140° C., up to 99% yield was quantified by GC. (Li, H.; He, J.; Riisager, A.; Saravanamurugan, S.; Song. B. and Yang, S. *ACS Catal.* 2016, 6, 7722-7727). Another CTH approach with NiO nanoparticles was performed and it was observed that the 5-MFA with 93% yield was obtained from 5-methylfurfural at high temperature at 180° C. (He, J.; Schill, L.; Yang, S. and Riisager, A., *ACS Sustainable Chem. Eng.,* 2018, 6, 17220-17229). Synthesis of 2-Methylfuran (MF) has also been reported recently by Zhao et al through selective Deoxygenation of Aqueous Furfural over $CuO/Cu_2O{\cdot}SiO_2$ sites via a Copper phyllosilicate precursor without extraneous gas (Li, B.; Li. L.; Sun, H. and Zhao, C. *ACS Sustainable Chem. Eng.,* 2018, 6, 12096-12103). Zhu et al reported that the Cu-based catalyst supported on $SiO_2$ selectively converted furfural to 2-MF in a high yield of 89% (Dong, F.; Zhu, Y. L.; Zheng, H. Y.; Zhu, Y. F.; Li, X. Q. and Li, Y. W. *J. Mol. Catal. A: Chem.* 2015, 398, 140-148). A hybrid catalytic approach was also applied for the synthesis of 2-MF from furfural by using Cu—Zn—Al catalyst and cyclohexanol as a hydrogen donor with a selectivity of 87% at 250° C. (Zheng. H. Y.; Zhu, Y. L.; Bai, Z. Q.; Huang. L.; Xiang. H. W. and Li, Y. W. *Green Chem.* 2006, 8 (1), 107-109).

In continuation to the prior-arts, the present invention is targeted to develop a very facile process for methyl substituted furan compounds from different aldehyde substituted furan compounds. The present development, particularly relates to a process for preparation of 5-methyl furfuryl alcohol (5-MFA), 2,5-dimehtyl furan (DMF), 2-methyl furan from their corresponding aldehyde compounds, having huge application as bio-fuel and other applications.

OBJECTIVE OF THE INVENTION

The main objective of the present invention is to provide 5-methyl substituted furan compounds of general formula (I).

(I)

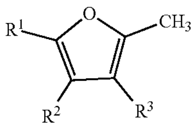

Yet another objective of the invention is to develop a metal and hydrogen gas free, highly selective and cost-effective process for 5-MFA and DMF synthesis from 5-HMF and 2,5-diformylfuran (DFF) or 5-methylfuran-2-carbaldehyde following convenient approaches having versatile applications in the area of bio-fuel, food additive, pharmaceuticals and obviates the drawbacks as detailed.

Yet another objective of the present invention is to develop an atom-economy and high yielding approach with very less by-product formation and without a need of tedious purification.

Yet another objective of the present invention is to develop a milder and efficient approach, applicable in scale-up transformation.

Yet another objective of the present invention is to develop scalable process for biofuel or bio-fuel candidate production utilizing low cost carbohydrates-based bio-waste, following stepwise approaches from 5-HMF or its aldehyde substituted derivatives.

Yet another objective of the present invention is to apply the same strategy for reduction of aldehyde group attached with similar type of molecules.

Yet another objective of the present invention is to utilize non-edible and low-cost cellulose/carbohydrates to high valued biochemical (5-MFA, DMF, etc.) production as a feedstock of bio-fuel, food additive, fragrances and pharmaceutical applications.

Yet another objective of the present invention is to utilize the 5-MFA to 2-(ethoxymethyl)-5-methylfuran (EMMF) production as a biofuel/bio-diesel and other commercial applications.

Yet another objective of the present invention is to process development for low cost 2,5-dimethyl furan (DMF) production as biofuel and commercially important molecules/products synthesis.

SUMMARY OF THE INVENTION

In an embodiment, the present invention provides a process for the preparation of 5-methyl substituted furans of general formula (I):

(I)

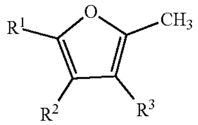

wherein;

- $R^1$ is selected from the group comprising: hydrogen, hydroxymethyl, methyl, alkyl, hydroxy, aldehyde, halide, ester, carboxylic acid, amide, amine, substituted amine, alkoxy/ether linkages, sulphur derivatives, phosphorous derivatives, and aryl and hetero aryl functionality; and $R^2$ and $R^3$ may be selected from the group comprising: hydrogen, alkyl, and aryl.

In another embodiment, the present invention provides a cost-effective, atom-economic, highly-selective and high yielding approach for the preparation of 5-methyl substituted furan compounds of general formula (I) from low cost carbohydrates (such as sugarcane bagasse, rice straw, corn cob, other cellulosic resources, cellulose, starch, polysaccharide, glucose and fructose) through 5-HMF and its corresponding products and minimization of by-product formation to avoid costly purification process.

In another embodiment, the present invention provides an one pot process for the preparation of 5-methyl substituted furans of general formula (I)

In another embodiment, the present invention provides a metal and hydrogen gas free, highly selective and cost-effective process for the preparation of 5-methyl substituted furans of general formula (I).

In another embodiment, the present invention provides a process for the preparation of 5-methyl substituted furans of general formula (I), comprising:

- i) reacting an amine compound and an inorganic base with substituted furfural of formula (II) in a suitable solvent to produce in situ corresponding imine (II)

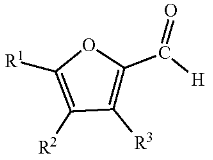

ii) reducing in situ generated imine of step (i) under basic condition in a suitable solvent to methyl substituted furans of general formula (I);

iii) isolating methyl substituted furans of general formula (I); and iv) optionally, purifying isolated methyl substituted furans of general formula (I).

In another embodiment, the present invention provides a process for the preparation of 5-methyl furfuryl alcohol (5-MFA) of formula (1), (III)

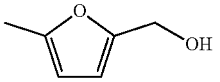

comprising:

i) reacting an amine compound and an inorganic base with 5-hydroxymethylfurfural (HMF) in a suitable solvent to produce in situ corresponding imine;

ii) reducing in situ generated imine of step (i) under basic condition in a suitable solvent to 5-MFA of formula (1);

iii) isolating 5-MFA of formula (1); and iv) optionally, purifying isolated 5-MFA.

In another embodiment, the present invention provides a process for the preparation of 2,5-dimethylfuran of formula (IV), (IV)

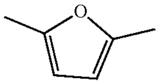

comprising the steps of:

i) reacting an amine compound and an inorganic base with 2,5-diformylfuran in a solvent to produce an in situ corresponding diimine;

ii) reducing the in situ generated diimine of step (i) under basic condition in a solvent to obtain the 2,5-dimethylfuran of formula (IV);

iii) isolating 2,5-dimethylfuran of formula (IV); and iv) optionally, purifying isolated 2,5-dimethylfuran of formula (IV).

In yet another embodiment, the present invention provides a process for the preparation of 2-(ethoxymethyl)-5-methylfuran (EMMF) of formula (V) from 5-methyl furfuryl alcohol (5-MFA) of formula (III).

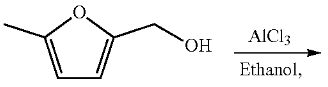

(III)

-continued

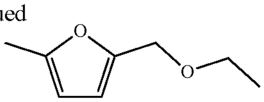

(V)

Accordingly, the method involves combination of inorganic bases under metal free milder solvent condition to avoid unwanted reaction and fulfill the desired condition required for successful conversion.

DETAILED DESCRIPTION OF THE INVENTION

Present invention provides "Metal free approaches for selective reduction of aldehyde to methyl group of different substituted furans" which comprises in situ steps following hydrazone of carbonyl compound and further decomposition in presence of strong base to give 5-methyl substituted furan compounds of general formula (I):

(I)

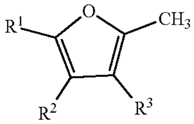

wherein;

$R^1$ is selected from the group comprising: hydrogen, hydroxymethyl, methyl, alkyl, hydroxy, formyl, halide, ester, carboxyl, nitro, amide, amino, substituted amino, alkoxy, ether, sulphur derivatives, phosphorous derivatives, and aryl and hetero aryl functionality; and $R^2$ and $R^3$ may be selected from the group comprising: hydrogen, alkyl, and aryl.

In contrast to the prior art processes, the present invention provides a method for metal and hydrogen gas free reduction method for direct conversion of 5-HMF and di/monoformyl furan to corresponding 5-MFA and DMF, with good yields.

The problematic and yet not been attempted Wolff-Kishner reduction approach has been performed under this study at comparably low temperature for selective conversion of 5-aldehyde substituted furan compounds to 5-methyl substituted furan compound of general formula (I) in good yield with negligible by-product formation.

Further, the process was performed under normal reflux condition without the need of high pressure autoclave system.

The modified synthetic approach was found to be highly selective, high yielding and applicable for large-scale production of 5-MFA with very good yield.

The whole modified system also restricts unwanted byproduct formation, over reduction and polymerization.

In an embodiment, the present invention provides a process for the preparation of 5-methyl substituted furans of general formula (I):

(I)

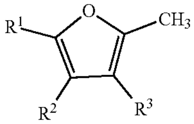

wherein;

$R^1$ is selected from the group comprising: hydrogen, hydroxymethyl, methyl, alkyl, hydroxy, aldehyde, halide, ester, carboxylic acid, amide, amine, substituted amine, alkoxy/ether linkages, sulphur derivatives, phosphorous derivatives, and aryl and hetero aryl functionality; $R^2$ and $R^3$ may be selected from the group comprising: hydrogen, alkyl, and aryl; the process comprising the steps of:

i) reacting an amine compound and an inorganic base with a substituted furfural of formula (II) in a solvent to obtain an in situ corresponding imine compound;

(II)

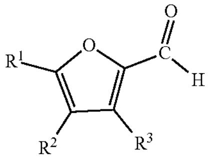

ii) reducing the in situ generated imine of step (i) under basic condition in a solvent to obtain the 5-methyl substituted furans of general formula (I);

iii) isolating methyl substituted furans of general formula (I); and iv) optionally, purifying isolated methyl substituted furans of general formula (I).

In another embodiment, the alkyl is methyl.

In another embodiment, the present invention provides a cost-effective, atom-economic, highly-selective and high yielding approach for the preparation of 5-methyl substituted furan compounds of general formula (I) from low cost carbohydrates (such as sugarcane bagasse, rice straw, corn cob, other cellulosic resources, cellulose, starch, polysaccharide, glucose and fructose) through 5-HMF and its corresponding products and minimization of by-product formation to avoid costly purification process.

In another embodiment, the present invention provides one pot process for the preparation of 5-methyl substituted furans of general formula (I)

In another embodiment, the present invention provides a metal and hydrogen gas free, highly selective and cost-effective process for the preparation of 5-methyl substituted furans of general formula (I).

In another embodiment, the present invention provides a process for the preparation of 5-methyl furfuryl alcohol (5-MFA) of formula (1), (III)

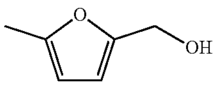

comprising:

i) reacting an amine compound and an inorganic base with 5-hydroxymethylfurfural (HMF) in a suitable solvent to produce in situ corresponding imine;

ii) reducing in situ generated imine of step (i) under basic condition in a suitable solvent to 5-MFA of formula (1);

iii) isolating 5-MFA of formula (III); and iv) optionally, purifying isolated 5-MFA of formula (III).

5-HMF has been used as a main building block, produced from carbohydrates for the construction of 5-MFA.

Alcoholic group of 5-HMF was not found to be reactive and ended with major 5-MFA product and 2,5-diformylfuran or monoformylfuran, both get converted successfully under this process to DMF as major product.

In another embodiment, the final product of formula (I) or formula (III) or formula (IV) are isolated by method of extraction employing suitable extracting solvent.

The suitable extracting solvent include but are not limited to alkyl ketones, ethyl acetate, dichloromethane, chloroform, THF and diethyl ether, or the like, and mixture thereof.

To achieve high yield and purity of final product of formula (I) or formula (III) or formula (IV) the distillation is performed at variable pressure and temperature condition.

The present process follows the traditional Wolff-Kishner reduction approach which was not yet been explored for aldehyde substituted furan compounds of general formula (II).

The amine compound includes but are not limited to hydrazine hydrate, hydrazine hydrochloride, aryl substituted hydrazine/alkyl substituted hydrazine/hydroxyl substituted hydrazine and further extended any such group of diamine compounds having the tendency of imine formation and follow the similar Wolff-Kishner reduction approach, or the like. Preferably, the inorganic base is a strong inorganic base.

The inorganic base includes, but are not limited to inorganic bases of alkoxy alkali metals, hydroxyl alkali metals and hydride alkali metals. Most preferably, the alkali metals are K, Na and Cs. The alkoxy alkali metals are selected from the group consisting of KO$^t$Bu, NaO$^t$Bu, KOEt, NaOEt, KOMe and NaOMe. The hydroxyl alkali metals are selected from the group consisting of NaOH and KOH; and the hydride alkali metal is NaH.

Most preferably, the inorganic base is selected from the group consisting of KO$^t$Bu, NaO$^t$Bu, KOEt, NaOEt, KOMe, NaOMe, NaOH, KOH and NaH.

Preferably, the suitable solvent is an alcoholic organic solvent.

The alcoholic organic solvent is any protonic alcohol with variable boiling points and having proton transfer capability with strong basic condition to reduce the in situ imine formed from carbonyls to alkyl carbon.

The alcoholic organic solvent includes, but are not limited to, alkyl alcohol, cyclic alkyl alcohols or the like.

Preferably, the alkyl or cyclic alkyl alcoholic solvent is selected from the group consisting of methanol, ethanol, iso-propanol, n-butanol, 2-butanol, t-butanol or mixture thereof. Most preferably, the alcoholic solvent is 2-butanol and ethanol.

The isolation step iii) of above processes is done by a method of extraction employing a solvent selected from the group consisting of alkyl ketones, ethyl acetate, dichloromethane, chloroform, THF, diethyl ether, or a mixture thereof.

In another embodiment of present invention, the methyl furfuryl alcohol (5-MFA) of formula (III) is further reacted in presence of aluminum trichloride and ethanol to obtain 2-(ethoxymethyl)-5-methylfuran (EMMF) of formula (V).

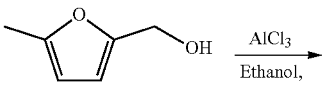

(III)

-continued

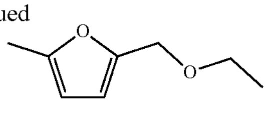

(V)

The suitable temperature for reaction may be variable from 80 to 180° C. based on different base and solvent applied for this transformation. Preferably, the reaction is performed at the temperature in the range from 120 to 140° C. to get highest yield with low by-product formation.

The reaction time may be selected from 2-6 hours or till completion of the reaction.

To enhance the scope of the present process, different 5-aldehyde substituted furan compounds have been used successfully for the production of 5-methyl substituted furans as proposed under the general formula (I).

In the process development different hydrazine analogues, inorganic bases and alcoholic solvents have been used for the selective formation of compounds proposed under general formula (I).

The present process for the preparation of the desired 5-methyl substituted furan of formula (I) in a highly selective manner involves use of amine compound for selective imine formation with aldehyde group of substituted furan compounds of formula (II). The base under alcoholic solvent condition specifically reduces the carbonyl group through proton transfer by producing nitrogen gas as one of the by-product.

Preferably, molar concentration/ratio of reactants is: aldehyde substituted furan (1 equiv.), amine compound (1-3 eqivs.), inorganic base (0.5-4 eqivs.).

The method of purification is selected from any suitable method known in the art, which include but is not limited to chromatography technique, distillation, crystallization etc.

Preferably, purification is performed by solvent extraction, fractional distillation and may be followed by other purification technique.

In yet another embodiment, the present invention provides a process for the preparation of 2-(ethoxymethyl)-5-methylfuran (EMMF) of formula (V) from 5-methyl furfuryl alcohol (5-MFA) of formula (III).

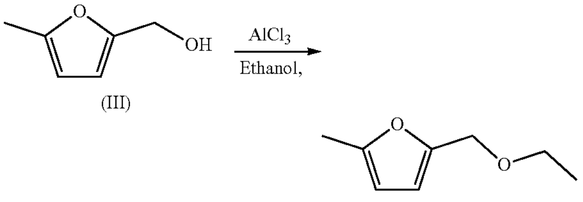

(III)

(V)

In the present process, the optimized reagents, substrates, solvents and reaction conditions altogether are playing significant role to produce the desired compounds of general formula (I) with minimized by-product formation.

Further, the present process is applicable for scale-up production of 5-methyl substituted furan compounds of general formula (I) from different aldehyde substituted furan compounds; which could be applicable as a feedstock for bio-fuel and other commercially valuable products.

The scalable process for the preparation of 5-MFA as feedstock chemical could further be useful as precursor of biofuel such as 2,5-dimethylfuran (2,5-DMF) and other important bio-chemicals production (Scheme 1).

Scheme 1. 5-MFA production from 5-HMF is a platform compound for biofuel and other important bio-chemicald production

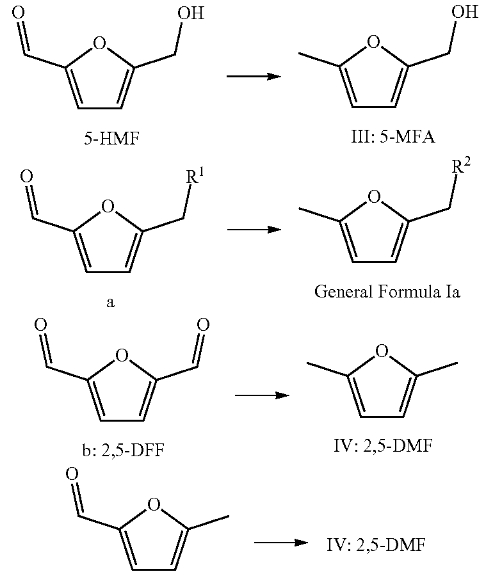

5-HMF

III: 5-MFA a

General Formula Ia b: 2,5-DFF

IV: 2,5-DMF c: 5-methyl-2-furfuraldehyde

IV: 2,5-DMF

List of Abbreviations

HMF: 5-hydroxymethylfurfural
DMF: 2,5-dimethylfuran
5-MFA: 5-methyl furfuryl alcohol
MF: 2-methylfuran
EMMF: 2-(ethoxymethyl)-5-methylfuran
THF: Tetrahydrofuran
GC-MS: Gas chromatography/Mass spectrometry
NMR: Nuclear magnetic resonance
TLC: Thin layer chromatography Material and Method Used in Experiments:

All the starting materials and solvents used were purchased from commercial suppliers such as Hydrazine hydrate and its analogs from Thomas Baker and Sigma, bases from Avra, solvents from CDH, SD Fine, the 5-HMF was used and prepared by our own patented process. (Application number: 201811023331) and other starting materials from Sigma and TCI.

EXAMPLES

General Experimental Procedure

An oven dried round bottomed flask (500 mL) was charged with base (0.5-2.0 eq.) and alcoholic solvent. The reaction mixture was heated at range of temperature 120° C. to 140° C. till the base completely got dissolved. In another round bottomed flask 5-HMF (1.0 eq.) was charged along with 2-butanol followed by the dropwise addition of hydrazine hydrate (1-3 eq.) with gentle agitation. 5-HMF mixture was added to the pre-dissolved basic solution gradually and refluxed at 120-130° C. for 2-6 hours. The progress of reaction was monitored by TLC and after completion of the reaction, the mixture was extracted by ethyl acetate/diethyl ether and dried over $Na_2SO_4$ followed by removal of solvent by distillation at 100-110° C. under vacuum gave crude product 5-MFA which further purified by vacuum distillation gave 5-MFA in 50-70% yield and >90% selectivity. The product was further analysed by GC-MS and NMR ($^1$H and $^{13}$C).

Scheme 2. Synthesis of 5-methylsubstituted furans from 5-aldehyde substituted furans

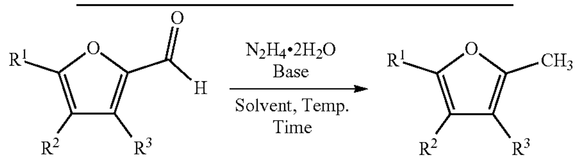

1. Experimental Procedure for 5-MFA Synthesis from 5-HMF

A dried batch reactor (15 L) was charged with KO$^t$Bu (106.8 g, 0.95 mol) and 2-butanol (1 L). The reaction mixture was heated, stirred and reflux at 130° C. till the base completely get dissolved. In another round bottomed flask, 5-HMF (100.0 g, 0.79 mol) was charged along with 2-butanol (300 mL) followed by the dropwise addition of hydrazine hydrate (78.0 mL, 1.58 mol) with gentle agitation. 5-HMF mixture was added to the pre-dissolved basic solution gradually and refluxed at 120-130° C. for 3-6 hours. The progress of the reaction was monitored by TLC and after completion of reaction, the mixture was extracted by ethyl acetate/diethyl ether and dried over $Na_2SO_4$ followed by removal of solvent by vacuum distillation at 100-110° C. gave 5-MFA, 45.15 g in 51% yield. The crude product was further analysed by GC-MS and NMR. $^1$H NMR (300 MHZ, $CDCl_3$) δ 6.15 (d, 1H, J=3 Hz), 5.91 (d, 1H, J=3 Hz), 4.52 (s, 2H), 2.29 (s, 3H); $^{13}$C NMR (300 MHZ, $CDCl_3$) δ 152.31, 152.30, 108.67, 106.19, 57.35, 13.48; GC-MS $[M]^+$ =112

Scheme 3. Synthesis of 5-MFA from 5-HMF

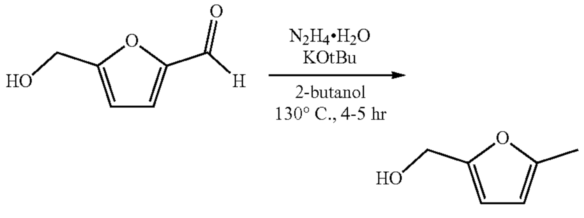

(III)

2. Experimental Procedure for 5-MFA Synthesis from 5-HMF

An oven dried round bottomed flask (500 mL) was charged with sodium tert. butoxide NaO$^t$Bu (18.2 g, 0.19 mol) and 2-butanol (25 mL). The reaction mixture was heated, stirred and reflux at 130° C. till base completely got dissolved. In another round bottomed flask HMF (20 g, 0.15 mmol) was charged along with 2-butanol (15 mL) followed by dropwise addition of hydrazine hydrate (11.6 mL, 0.23 mol), with gentle agitation. 5-HMF mixture was added to the pre-dissolved basic solution gradually and refluxed at 120-130° C. for 3-6 hours. The progress of reaction was monitored by TLC and after completion of reaction the mixture was extracted by ethyl acetate/diethyl ether and dried over $Na_2SO_4$ followed by removal of solvent by distillation at 100-110° C. gave crude product 5-MFA which further purified by vacuum distillation gave 5-MFA, 9.0 g in 50.5% yield. The distilled reaction residue was further analysed by GC-MS and NMR. The spectral data was same as mentioned in scheme 2, compound III.

Scheme 4. Synthesis of 5-MFA from 5-HMF

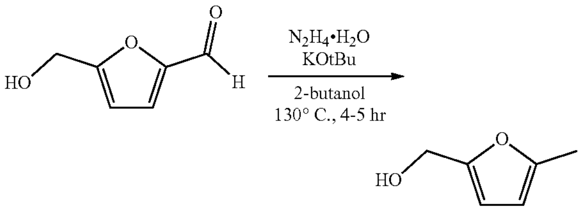

(III)

3. Experimental Procedure for 5-MFA Synthesis from 5-HMF

An oven dried round bottomed flask (250 mL) was charged with KOH (3.3 g, 0.05 mol) and 2-butanol (10 mL). The reaction mixture was heated, stirred and reflux at 130° C. till base completely got dissolved. In another round bottomed flask HMF (5.0 g, 0.03 mol) was charged along with 2-butanol (10 mL) followed by dropwise addition of hydrazine hydrate (2.9 mL, 0.05 mol) with gentle agitation. 5-HMF mixture was added to the pre-dissolved basic solution gradually and refluxed at 120-130° C. for 3-6 hours. The progress of reaction was monitored by TLC and after completion of reaction the mixture was extracted by ethyl acetate/diethyl ether and dried over $Na_2SO_4$ followed by removal of solvent by distillation at 100-110° C. gave crude product 5-MFA which further purified by vacuum distillation gave 5-MFA, 1.1 g in 25% yield. The distilled reaction residue was further analysed by GC-MS and NMR. The spectral data was same as mentioned in scheme 2, compound III.

Scheme 5. Synthesis of 5-MFA from 5-HMF

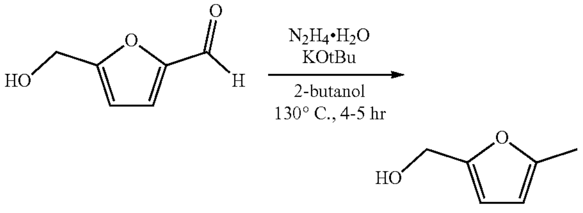

(III)

4. Experimental Procedure for 2-methylfuran Synthesis from 2-furfuraldehyde

An oven dried round bottomed flask (100 mL) was charged with KO$^t$Bu (1.1 g, 0.010 mol) and 2-butanol (3 mL). The reaction mixture was heated, stirred and reflux at 130° C. till base completely got dissolved. In another round bottomed flask 2-furfuraldehyde (1.0 g, 0.01 mol) was charged along with 2-butanol (3 mL) followed by dropwise addition of hydrazine hydrate (1.02 mL, 0.020 mol) with gentle agitation. 2-furfuraldehyde mixture was added to the pre-dissolved basic solution gradually and refluxed at 120-130° C. for 3-6 hours. The progress of reaction was monitored by TLC and after completion of reaction the mixture was analysed by GC-MS. The product was further analysed by GC-MS and compare with standard.

Scheme 6. Synthesis of 2-methylfuran from 2-furfuraldehyde

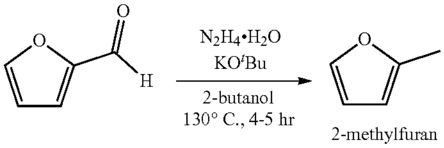

2-methylfuran

5. Experimental Procedure for 2,5-dimethylfuran (DMF) Synthesis from 2,5-diformylfuran An oven dried round bottomed flask (100 mL) was charged with $KO^tBu$ (45.0 mg, 0.403 mmol) and 2-butanol (1.5 mL). The reaction mixture was heated, stirred and reflux at 130° C. till base completely got dissolved. In another round bottomed flask 2,5-diformylfuran (100 mg, 0.806 mmol) was charged along with 2-butanol (3 mL) followed by dropwise addition of hydrazine hydrate (79 µL, 1.612 mmol) with gentle agitation. 2,5-diformylfuran mixture was added to the pre-dissolved basic solution gradually and refluxed at 130° C. for 3-5 hours. The progress of reaction was monitored by TLC and after completion of reaction the mixture was analysed by GC-MS. The product was further analysed by GC-MS and compared with standard.

Scheme 7. Synthesis of 2,5-Dimethylfuran from 2,5-Diformylfuran

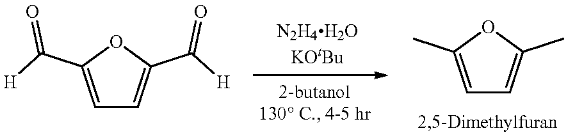

2,5-Dimethylfuran

6. Experimental Procedure for 2-ethyl-5-methylfuran Synthesis from 5-ethylfuran-2-carbaldehyde An oven dried round bottomed flask (100 mL) was charged with $KO^tBu$ (45.0 mg, 0.403 mmol) and 2-butanol (1.5 mL). The reaction mixture was heated, stirred and reflux at 130° C. till base completely got dissolved. In another round bottomed flask 5-ethylfuran-2-carbaldehyde (100 mg, 0.805 mmol) was charged along with 2-butanol (3 mL) followed by dropwise addition of hydrazine hydrate (79 µL, 1.611 mmol) with gentle agitation. 5-Ethylfuran-2-carbaldehyde mixture was added to the pre-dissolved basic solution gradually and refluxed at 120-130° C. for 3-5 hours. The progress of reaction was monitored by TLC and after completion of reaction the mixture was analysed by GC-MS and compared with standard.

Scheme 8. Synthesis of 2-ethyl-5-methylfuran from 5-ethylfuran-2-carbaldehyde.

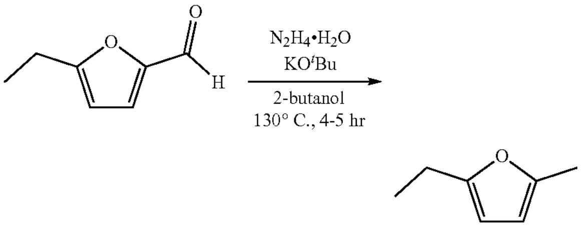

2-ethyl-5-methylfuran

7. Experimental Procedure for 4,5-dimethylfuran-2-carbaldehyde Synthesis

An oven dried round bottomed flask (100 mL) was charged with $KO^tBu$ (45.0 mg, 0.403 mmol) and 2-butanol (1.5 mL). The reaction mixture was heated, stirred and reflux at 130° C. till base completely got dissolved. In another round bottomed flask 4,5-dimethylfuran-2-carbaldehyde (100 mg, 0.806 mmol) was charged along with 2-butanol (3 mL) followed by dropwise addition of hydrazine hydrate (79 µL, 1.612 mmol) with gentle agitation. 4,5-dimethylfuran-2-carbaldehyde mixture was added to the pre-dissolved basic solution gradually and refluxed at 120-130° C. for 3-5 hours. The progress of reaction was monitored by TLC and after completion of reaction the mixture was analysed by GC-MS and compared with standard.

Scheme 9. Synthesis of 2,3,5-trimethylfuran from 4,5-dimethylfuran-2-carbaldehyde

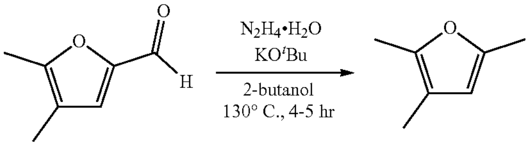

2,3,5-trimethylfuran

8. Experimental Procedure for 2-(ethoxymethyl)-5-methylfuran (EMMF) Synthesis from 5-MFA An oven dried round bottomed flask (100 mL) was charged with 5-MFA (100 mg, 0.8919 mmol) and ethanol (2 mL) followed by the addition of aluminium trichloride (3.56 mg, 0.0267 mmol). Heat and stirred the reaction mass under reflux at 90° C. for 4-12 hr. The progress of the reaction was monitored by TLC and after completion of the reaction the reaction mixture was neutralized with sodium bicarbonate followed by the extraction with diethyl ether/ethyl acetate. The extract of the reaction was dried over sodium sulphate and concentrated under vacuum to get desired product compound V with approximately quantitative conversion. The product was further analysed by GC-MS and compared with standard.

Scheme 10. Synthesis of EMMF from 5-MFA

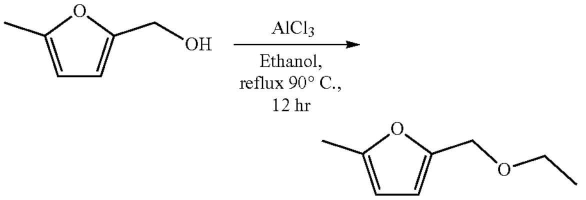

(V)

The main advantages of the present invention are:

1. A simple, atom-economy and cost-effective process has been developed for the preparation of 5-methyl substituted furans from 5-aldehyde substituted furans.
2. Under this process no hydrogen gas and metal has been used and easy to scale-up and no need of tedious purification to achieve high yield.
3. No over reduction was noticed under this process and product separation is easy by solvent extraction and distillation.
4. No need of high-pressure autoclave system and the reaction performed under reflux condition therefore reduces the risk.
5. The process could be applicable for low cost production of highly demanding platform compound 5-MFA, 2,5-DMF and other 5-methyl substituted furan compounds as a biofuel and other applications.
6. 5-MFA is a very good choice for 2,5-DMF production following energy efficient process.
7. Etherification of 5-MFA can be done under milder acidic condition with different alkyl alcohols having huge application as biofuel and bio-diesel.

We claim:

1. A process for the preparation of a 5-methyl substituted furan of general formula (I):

(I)

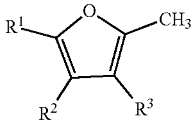

where:

$R^1$ is selected from the group consisting of hydrogen, hydroxymethyl, alkyl, hydroxy, aldehyde, halide, ester, carboxyl, nitro, amino, amide, substituted amino, alkoxy/ether linkages, sulfur derivatives, phosphorous derivatives, aryl, and heteroaryl; and $R^2$ and $R^3$ are selected from the group consisting of hydrogen, alkyl, and aryl, the process comprising:

(i) reacting an amine compound and an inorganic base with a substituted furfural in an alcoholic organic solvent selected from alkyl alcohols or cyclic alkyl alcohols at a reaction temperature from 120° C. to 140° C. for a reaction time period from 2 hours to 6 hours to obtain an in situ generated corresponding imine compound, the substituted furfural having formula (II):

(II)

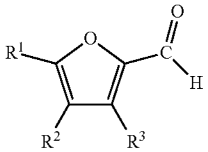

where $R^1$, $R^2$, and $R^3$ of formula (II) are as defined in general formula (I);

(ii) reducing the in situ generated corresponding imine compound of (i) under basic conditions in the alcoholic organic solvent to obtain a 5-methyl substituted furan of general formula (I);

(iii) isolating the 5-methyl substituted furan; and (iv) optionally, purifying the isolated 5-methyl substituted furan.

2. The process according to claim 1, wherein the amine compound is selected from the group consisting of hydrazine hydrate, hydrazine hydrochloride, aryl substituted hydrazine, alkyl substituted hydrazine, hydroxyl substituted hydrazine, and mixtures thereof.

3. The process according to claim 1, wherein the inorganic base is chosen from alkali metal alkoxides, alkali metal hydroxides, or alkali metal hydrides.

4. The process according to claim 1, wherein the inorganic base is selected from the group consisting of $KO^tBu$, $NaO^tBu$, KOEt, NaOEt, KOMe, NaOMe, NaOH, KOH, NaH, and mixtures thereof.

5. The process according to claim 1, wherein the alcoholic organic solvent has under the basic conditions a proton transfer capability sufficient to reduce the in situ corresponding imine compound.

6. The process according to claim 1, wherein the alcoholic organic solvent is selected from the group consisting of methanol, ethanol, isopropanol, n-butanol, 2-butanol, t-butanol, and mixtures thereof.

7. The process according to claim 1, wherein (iii) comprises extracting the 5-methyl substituted furan with a solvent selected from the group consisting of alkyl ketones, ethyl acetate, dichloromethane, chloroform, tetrahydrofuran, diethyl ether, and mixtures thereof.

8. The process according to claim 1, wherein (i) comprises reacting from 1 to 3 molar equivalents of the amine compound and from 0.5 to 4 molar equivalents of the inorganic base with 1 molar equivalent of the substituted furfural of formula (II).

9. The process according to claim 1, wherein:

the substituted furfural of formula (II) is 5-hydroxymethylfurfural of formula (IIIa):

(IIIa)

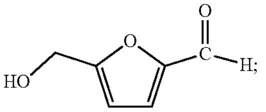

and the 5-methyl substituted furan of general formula (I) is 5-methyl furfuryl alcohol of formula (III):

(III)

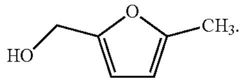

10. The process according to claim 9, wherein the amine compound is selected from the group consisting of hydrazine hydrate, hydrazine hydrochloride, aryl substituted hydrazine, alkyl substituted hydrazine, hydroxyl substituted hydrazine, and mixtures thereof.

11. The process according to claim 9, wherein the inorganic base is selected from the group consisting of $KO^tBu$, $NaO^tBu$, KOEt, NaOEt, KOMe, NaOMe, NaOH, KOH, NaH, and mixtures thereof.

12. The process according to claim 9, wherein the alcoholic organic solvent is selected from the group consisting of methanol, ethanol, isopropanol, n-butanol, 2-butanol, t-butanol, and mixtures thereof.

13. The process according to claim 9, wherein (iii) comprises extracting the 5-methyl substituted furan with a solvent selected from the group consisting of alkyl ketones, ethyl acetate, dichloromethane, chloroform, tetrahydrofuran, diethyl ether, and mixtures thereof.

14. The process according to claim 9, wherein (i) comprises reacting from 1 to 3 molar equivalents of the amine compound and 0.5 to 2 molar equivalents of the inorganic base with 1 molar equivalent of the 5-hydroxymethylfurfural.

15. The process according to claim 9, further comprising reacting the 5-methyl furfuryl alcohol in the presence of aluminum trichloride and ethanol to obtain 2-(ethoxymethyl)-5-methylfuran of formula (V):

(V)

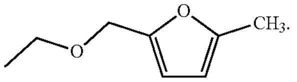

16. The process according to claim 1, wherein:
the substituted furfural of formula (II) is 2,5-diformylfuran of formula (IVa):

(IVa)

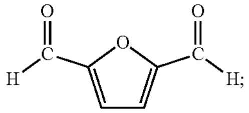

the reaction temperature is 130° C.;
the reaction time period is from 3 hours to 5 hours;
the in situ generated corresponding imine compound is a diimine; and
the 5-methyl substituted furan of general formula (I) is 2,5-dimethylfuran of formula (IV):

(IV)

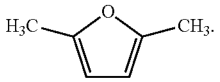

17. The process according to claim 16, wherein the amine compound is selected from the group consisting of hydrazine hydrate, hydrazine hydrochloride, aryl substituted hydrazine, alkyl substituted hydrazine, hydroxyl substituted hydrazine, and mixtures thereof.

18. The process according to claim 16, wherein the inorganic base is selected from the group consisting of $KO^tBu$, $NaO^tBu$, KOEt, NaOEt, KOMe, NaOMe, NaOH, KOH, NaH, and mixtures thereof.

19. The process according to claim 16, wherein the alcoholic organic solvent is selected from the group consisting of methanol, ethanol, isopropanol, n-butanol, 2-butanol, t-butanol, and mixtures thereof.

20. The process according to claim 16, wherein (i) comprises reacting 2 molar equivalents of the amine compound and 0.5 molar equivalents of the inorganic base with 1 molar equivalent of the 2,5-diformylfuran.

* * * * *